(12) United States Patent
Bandi et al.

(10) Patent No.: US 12,378,281 B2
(45) Date of Patent: Aug. 5, 2025

(54) TRITERPENONE DERIVATIVES AS HIV INHIBITORS

(71) Applicant: HETERO LABS LIMITED, Balanagar Hyderabad (IN)

(72) Inventors: Parthasaradhi Reddy Bandi, Balanagar Hyderabad (IN); Rathnakar Reddy Kura, Balanagar Hyderabad (IN); Panduranga Reddy Adulla, Balanagar Hyderabad (IN); V L Subrahmanyam Lanka, Balanagar Hyderabad (IN)

(73) Assignee: HETERO LABS LIMITED, Balanagar Hyderabad (IN)

( * ) Notice: Subject to any disclaimer, the term of this patent is extended or adjusted under 35 U.S.C. 154(b) by 977 days.

(21) Appl. No.: 17/430,116

(22) PCT Filed: Feb. 11, 2020

(86) PCT No.: PCT/IB2020/051050
§ 371 (c)(1),
(2) Date: Aug. 11, 2021

(87) PCT Pub. No.: WO2020/165742
PCT Pub. Date: Aug. 20, 2020

(65) Prior Publication Data
US 2022/0144882 A1 May 12, 2022

(30) Foreign Application Priority Data
Feb. 11, 2019 (IN) .............................. 201941005229

(51) Int. Cl.
*C07J 63/00* (2006.01)
*A61P 31/18* (2006.01)

(52) U.S. Cl.
CPC .............. *C07J 63/008* (2013.01); *A61P 31/18* (2018.01)

(58) Field of Classification Search
CPC ......... C07J 63/008; A61P 31/18; A61P 11/00; A61P 29/00; A61P 31/12; A61P 31/14
USPC ........................................................ 514/176
See application file for complete search history.

(56) References Cited

U.S. PATENT DOCUMENTS

| 10,533,035 B2 * | 1/2020 | Parthasaradhi Reddy .................. C07J 63/008 |
| 11,034,718 B2 * | 6/2021 | Parthasaradhi Reddy .................. C07J 63/008 |
| 2017/0008921 A1 * | 1/2017 | Reddy ..................... A61P 31/18 |

FOREIGN PATENT DOCUMENTS

| WO | 2016178092 A2 | 11/2016 | |
| WO | WO-2017115329 A1 * | 7/2017 | ............ C07J 63/008 |
| WO | 2018029604 A1 | 2/2018 | |
| WO | WO-2018029610 A1 * | 2/2018 | ............ C07J 63/008 |
| WO | 2018065930 A1 | 4/2018 | |
| WO | WO-2018069857 A1 * | 4/2018 | ............ C07J 63/008 |

OTHER PUBLICATIONS

International Search Report of Application No. PCT/IB2020/051050; International Filing Date—Feb. 11, 2020; Date of Mailing—Jun. 23, 2020, 4 pages.
Written Opinion of International Application No. PCT/IB2020/051050; International Filing Date—Feb. 11, 2020; Date of Mailing—Jun. 23, 2020, 7 pages.
Extended European Search Report for EP Application No. 20756356.0; Applicant—Hetero Labs Limited; Dated—Sep. 22, 2022, 10 pages.

* cited by examiner

*Primary Examiner* — Amy L Clark
*Assistant Examiner* — Liyuan Mou
(74) *Attorney, Agent, or Firm* — CANTOR COLBURN LLP

(57) ABSTRACT

The present invention relates to novel triterpenone derivatives of formula (I); and pharmaceutically acceptable salts thereof, wherein $R_1$, $R_2$, $R_3$, $R_4$, $R_5$ and $R_6$ are as defined herein. The invention also relates to novel triterpenone derivatives, related compounds, and pharmaceutical compositions useful for the therapeutic treatment of viral diseases and particularly HIV mediated diseases.

(I)

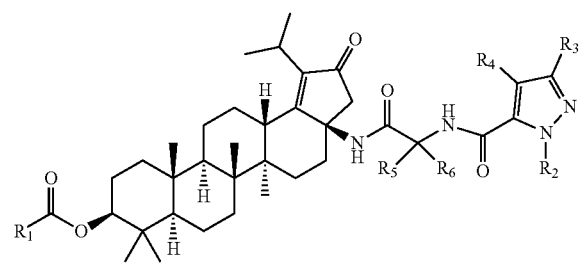

5 Claims, No Drawings

TRITERPENONE DERIVATIVES AS HIV INHIBITORS

CROSS REFERENCE TO RELATED APPLICATIONS

This application is a National Stage application of PCT/IB2020/051050, filed Feb. 11, 2020 which claims the benefit of Indian provisional application no. 201941005229, filed Feb. 11, 2019, which is hereby incorporated by reference in its entirety.

FIELD OF THE INVENTION

The present invention relates to novel triterpenone derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220,868-871; N. Eng. J. Med. 1984, 311, 1292-1297). AIDS is characterized by the destruction of the immune system, particularly of CD4+T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996,39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004,78(2): 922-9; J. Biol. Chem. 2005,280(51):42149-55; J. Virol. 2006,80(12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO2018/069857 describes C-3 novel triterpenone with C-17 reverse amide heterocycle derivatives; WO2018/065930 describes C-3 novel triterpenone with C-17 reverse amide derivatives; WO2018/029610 describes C-3 novel triterpenone with C-17 N-amide derivatives; WO2018/029604 describes C-3 novel triterpenone with C-17 reverse amide derivatives; WO2017/064628 describes C-3 novel triterpenone with C-17 urea derivatives; WO2016/178092 describes C-3 novel triterpenone with C-17 reverse amide derivatives; WO2016/077561 describes oxolupene derivatives; WO2014/093941 describes pharmaceutical compositions of betulin derivatives; WO2013/117137 describes lupane triterpenoids derivatives and pharmaceutical use thereof; WO2013/020245 describes carbonyl derivatives of betulin; WO2013/090664 describes preparation of betulin derivatives for the treatment of HIV; WO2013/091144 describes preparation of propenoate derivatives of betulin useful for the treatment of HIV; WO2013/090683 describes preparation of betulin propenoate derivatives for the treatment of HIV; WO2011/100308 describes preparation of betulin derivatives for treatment of HIV-1; WO2009/082819 describes preparation of 17-amino lupane derivatives as anti-HIV agents; WO2009/082818 describes preparation of C21-keto lupane derivatives for the treatment of HIV infections.

Some additional references disclose betulinic acid related compounds. For example, WO2007/141383 describes betulin derivatives as antifeedants for plant pests; WO 2007/141392 describes cosmetic and pharmaceutical compositions comprising betulonic acid and betulin derivatives; U.S. Pat. No. 6,670,345 describes use of betulinic acid and its derivatives for inhibiting cancer growth and process for the manufacture of betulinic acid; WO2002/091858 describes anxiolytic marcgraviaceae compositions containing betulinic acid, betulinic acid derivatives, and methods of preparation and use; Pharmaceutical Chemistry Journal, 2002, 36(9), 29-32 describes synthesis and anti-inflammatory activity of new acylated betulin derivatives, and WO2000/046235 describes preparation of novel betulinic acid derivatives for use as cancer growth inhibitors.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compound of the formula (I)

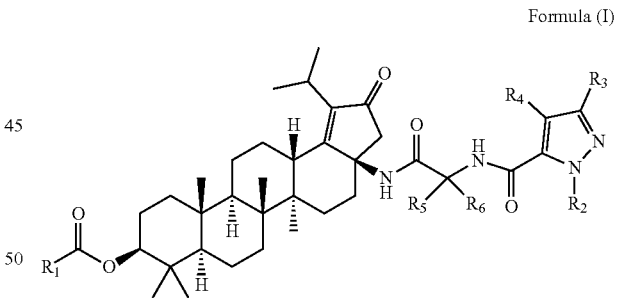

Formula (I)

wherein,
$R_1$ is

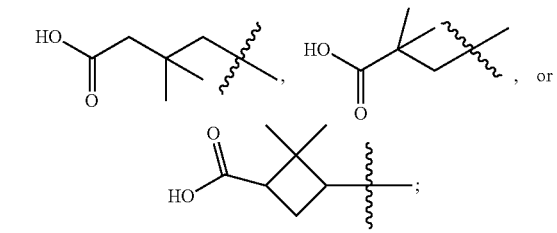

, or ;

R₂ is selected from hydrogen, C₁-C₆ alkyl, —C(O)OR_a, —(CH₂)₁₋₂—O—P(O)—(OR_a)₂, —C(O)-alkoxy, —C(O)-dialkylaminoalkyl, dialkylaminoalkyl, —(CH₂)₁₋₄-heterocyclyl, or —C(O)—(CH₂)₁₋₄-heterocyclyl;

R₃ is selected from halo, haloalkyl, optionally substituted alkoxy, optionally substituted amino, optionally substituted aminoalkyl, optionally substituted cycloalkyl, —C(O)OR_a, optionally substituted aryl, optionally substituted heterocyclyl, optionally substituted heteroaryl or —S(O)₂R_a; wherein the optional substituents are alkyl, halo, or haloalkyl;

R⁴ is hydrogen, or selected from hydroxyl, hydroxyalkyl, halo, haloalkyl, optionally substituted alkoxy, optionally substituted amino, optionally substituted aminoalkyl, optionally substituted cycloalkyl, —C(O)OR_a, optionally substituted aryl, optionally substituted heterocyclyl, optionally substituted heteroaryl, or —S(O)₂R_a;

R₅ and R₆ are selected from alkyl, or R₅ and R₆ are taken together with the carbon atom to which they are attached to form cycloalkyl, or optionally substituted heterocyclyl; wherein the optional substituent is alkyl, or —C(O)OR_a; and R_a is selected from hydrogen, alkyl, or heterocyclyl; or pharmaceutically acceptable salts, stereoisomers, prodrugs, or combination thereof.

According to one embodiment, there is provided a compound of formula (I), wherein R₁ is

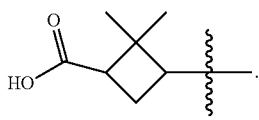 [SMILES: *C1CC(C(=O)O)C1(C)C]

According to another embodiment, there is provided a compound of formula (I), wherein R₂ is hydrogen.

According to yet another embodiment, there is provided a compound of formula (I), wherein R₂ is —C(O)OR_a; wherein R_a is ethyl.

According to yet another embodiment there is provided a compound of formula (I), wherein R₃ is phenyl.

According to yet another embodiment there is provided a compound of formula (I), wherein R₃ is trifluoromethane.

According to yet another embodiment there is provided a compound of formula (I), wherein R₄ is hydrogen.

According to yet another embodiment there is provided a compound of formula (I), wherein R₅ and R₆ are methyl.

Accordingly, another aspect of the present invention provides compound of formula (IA):

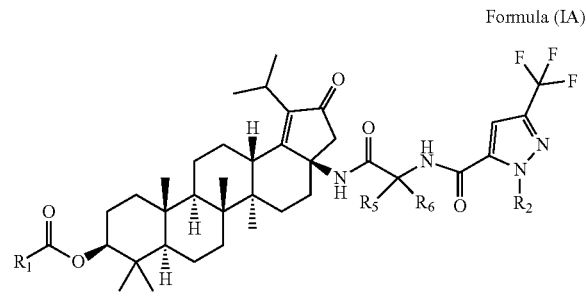

Formula (IA)

wherein,

R₁, R₂, R₅ and R₆ are same as defined in formula (I); or pharmaceutically acceptable salts, pharmaceutically acceptable stereoisomers, prodrugs, or combination thereof.

According to one embodiment, there is provided a compound of formula (I), wherein R₁ is

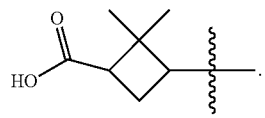 [SMILES: *C1CC(C(=O)O)C1(C)C]

According to another embodiment, there is provided a compound of formula (I), wherein R₂ is hydrogen.

According to yet another embodiment, there is provided a compound of formula (I), wherein R₂ is —C(O)OR_a; wherein R_a is ethyl.

According to yet another embodiment there is provided a compound of formula (I), wherein R₅ and R₆ are methyl.

Accordingly, to yet another aspect of the present invention provides compound of formula (IB):

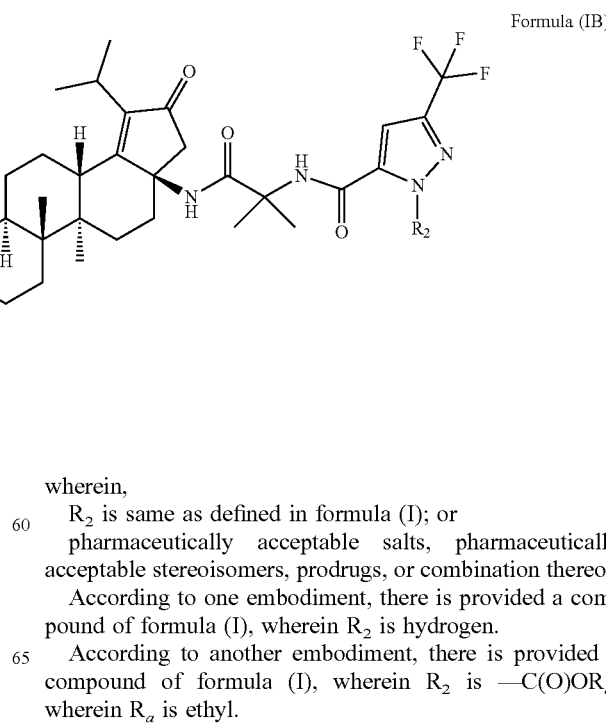

Formula (IB)

wherein,

R₂ is same as defined in formula (I); or pharmaceutically acceptable salts, pharmaceutically acceptable stereoisomers, prodrugs, or combination thereof.

According to one embodiment, there is provided a compound of formula (I), wherein R₂ is hydrogen.

According to another embodiment, there is provided a compound of formula (I), wherein R₂ is —C(O)OR_a; wherein R_a is ethyl.

In a further embodiment, there is provided a method for treating mammals infected with a virus, especially wherein said virus is HIV, comprising administering to said mammal an antiviral effective amount of a compound which is selected from the group of compounds of formula (I), and one or more pharmaceutically acceptable carriers, excipients or diluents. Optionally, the compound of formula (I) can be administered in combination with an antiviral effective amount of another AIDS treatment agent selected from the group consisting of: (a) an AIDS antiviral agent or (b) an anti-infective agent.

Another embodiment of the present invention is a pharmaceutical composition comprising one or more compounds of formula (I), and one or more pharmaceutically acceptable carriers, excipients, and/or diluents; and optionally in combination with another AIDS treatment agent selected from the group consisting of: AIDS antiviral agent or anti-infective agent.

In another embodiment of the invention there is provided one or more methods for preparation of the compounds of formula (I).

In one further embodiment, the present invention also encompasses the method(s) of preparation of intermediates used in the preparation of compound of formula (I).

Below are the representative compounds, which are illustrative in nature only and are not intended to limit to the scope of the invention (Nomenclature has been generated from ChemBioDraw Ultra 13.0 version):

(1R,3S)-3-((((3aR,5aR,5bR,7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(ethoxycarbonyl)-3-(trifluoromethyl)-1H-pyrazole-5-carboxamido)-2-methylpropanamido)-1-isopropyl-5a, 5b, 8,8,11a-pentamethyl-2-oxo-3,3a,4,5,5a,5b,6,7,7a,8,9, 10,11,11a,11b,12,13, 13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(3-phenyl-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8,9,10,11,11a,11b,12, 13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(2-(1-(methoxycarbonyl)-3-(trifluoromethyl)-1H-pyrazole-5-carboxamido)-2-methylpropanamido)-5a,5b,8,8,11a-pentamethyl-2-oxo-3,3a,4,5,5a,5b,6, 7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(((dimethoxyphosphoryl)oxy)methyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-((phosphonooxy)methyl)-3-(trifluoromethyl)-1H-pyrazole-5-carboxamido)propanamido)-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(2-(1-((2-methoxyethoxy)carbonyl)-3-(trifluoromethyl)-1H-pyrazole-5-carboxamido)-2-methylpropanamido)-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(2-(1-((2-(2-methoxyethoxy)ethoxy)carbonyl)-3-(trifluoromethyl)-1H-pyrazole-5-carboxamido)-2-methylpropanamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(3-(dimethylamino)propanoyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(3-(dimethylamino)propyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(2-(dimethylamino)ethyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-(2-morpholinoethyl)-3-(trifluoromethyl)-1H-pyrazole-5-carboxamido)propanamido)-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-(2-(piperazin-1-yl)ethyl)-3-(trifluoromethyl)-1H-pyrazole-5-carboxamido)propanamido)-2-oxo-3,3a, 4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(1-(2-(1,1-dioxidothiomorpholino)ethyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-

(3-morpholinopropanoyl)-3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-(2-(piperazin-1-yl)acetyl)-3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(1-((piperidin-4-yloxy)carbonyl)-3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(1-(3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-(methoxycarbonyl)-3-(trifluoromethyl)-1H-pyrazole-5-carboxamido)cyclopropane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(((dimethoxyphosphoryl)oxy)methyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-((phosphonooxy)methyl)-3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-((2-methoxyethoxy)carbonyl)-3-(trifluoromethyl)-1H-pyrazole-5-carboxamido)cyclopropane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-((2-(2-methoxyethoxy)ethoxy)carbonyl)-3-(trifluoromethyl)-1H-pyrazole-5-carboxamido)cyclopropane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(3-(dimethylamino)propanoyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(3-(dimethylamino)propyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(2-(dimethylamino)ethyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(1-(1-(2-morpholinoethyl)-3-(trifluoromethyl)-1H-pyrazole-5-carboxamido)cyclopropane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-(2-(piperazin-1-yl)ethyl)-3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(2-(1,1-dioxidothiomorpholino)ethyl)-3-(trifluoromethyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(1-(1-(3-morpholinopropanoyl)-3-(trifluoromethyl)-1H-pyrazole-5-carboxamido)cyclopropane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-(2-(piperazin-1-yl)acetyl)-3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-

((piperidin-4-yloxy)carbonyl)-3-(trifluoromethyl)-1H-pyrazole-5-carboxamido)cyclopropane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(1-(3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-(methoxycarbonyl)-3-(trifluoromethyl)-1H-pyrazole-5-carboxamido)cyclobutane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(((dimethoxyphosphoryl)oxy)methyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-((phosphonooxy)methyl)-3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-((2-methoxyethoxy)carbonyl)-3-(trifluoromethyl)-1H-pyrazole-5-carboxamido)cyclobutane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-((2-(2-methoxyethoxy)ethoxy)carbonyl)-3-(trifluoromethyl)-1H-pyrazole-5-carboxamido)cyclobutane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(3-(dimethylamino)propanoyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(3-(dimethylamino)propyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(2-(dimethylamino)ethyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(1-(1-(2-morpholinoethyl)-3-(trifluoromethyl)-1H-pyrazole-5-carboxamido)cyclobutane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-(2-(piperazin-1-yl)ethyl)-3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(2-(1,1-dioxidothiomorpholino)ethyl)-3-(trifluoromethyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(1-(1-(3-morpholinopropanoyl)-3-(trifluoromethyl)-1H-pyrazole-5-carboxamido)cyclobutane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-(2-(piperazin-1-yl)acetyl)-3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(1-((piperidin-4-yloxy)carbonyl)-3-(trifluoromethyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(3-(3-(trifluoromethyl)-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(3-(3-(trifluoromethyl)-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(3-(1-(ethoxycarbonyl)-3-(trifluoromethyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(3-(1-(((dimethoxyphosphoryl)oxy)methyl)-3-(trifluoromethyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-((phosphonooxy)methyl)-3-(trifluoromethyl)-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-3a-(3-(1-((2-methoxyethoxy)carbonyl)-3-(trifluoromethyl)-1H-pyrazole-5-carboxamido)azetidine-3-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-(2-(piperazin-1-yl)acetyl)-3-(trifluoromethyl)-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-((piperidin-4-yloxy)carbonyl)-3-(trifluoromethyl)-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(1-(tert-butoxycarbonyl)-3-(3-(trifluoromethyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-3a-(1-methyl-3-(3-(trifluoromethyl)-1H-pyrazole-5-carboxamido)azetidine-3-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(3-(trifluoromethyl)-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-(((((3aR,5aR,5bR,7aR,9S,11aR,11bR,13aS)-1-isopropyl-5a,5b,8,8,11a-pentamethyl-2-oxo-3a-(3-(3-(trifluoromethyl)-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(3-(1-(ethoxycarbonyl)-3-(trifluoromethyl)-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(3-(1-(((dimethoxyphosphoryl)oxy)methyl)-3-(trifluoromethyl)-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-((phosphonooxy)methyl)-3-(trifluoromethyl)-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-3a-(3-(1-((2-methoxyethoxy)carbonyl)-3-(trifluoromethyl)-1H-pyrazole-5-carboxamido)oxetane-3-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-(2-(piperazin-1-yl)acetyl)-3-(trifluoromethyl)-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-5a,5b,8,8,11a-pentamethyl-2-oxo-3a-(3-(1-((piperidin-4-yloxy)carbonyl)-3-(trifluoromethyl)-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-(((((3aR,5aR,5bR,7aR,9S,11aR,11bR,13aS)-1-isopropyl-5a,5b,8,8,11a-pentamethyl-3a-(2-methyl-2-(3-phenyl-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-1-isopropyl-3a-(2-(1-(methoxycarbonyl)-3-phenyl-1H-pyrazole-5-carboxamido)-2-methylpropanamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-(((((3aR,5aR,5bR,7aR,9S,11aR,11bR,13aS)-3a-(2-(1-(ethoxycarbonyl)-3-phenyl-1H-pyrazole-5-carboxamido)-2-methylpropanamido)-1-isopropyl-5a,5b,8,8,
11a-pentamethyl-2-oxo-3,3a,4,5,5a,5b,6,7,7a,8,9,10,11,
11a,11b,12,13,13a-octadecahydro-2H-cyclopenta[a]
chrysen-9-yl)oxy)carbonyl)-2,2-dimethylcyclobutane-1-
carboxylic acid,
(1R,3S)-3-((((3aR,5aR,5bR,7aR,9S,11aR,11bR,13aS)-3a-
(2-(1-(ethoxycarbonyl)-3-(p-tolyl)-1H-pyrazole-5-car-
boxamido)-2-methylpropanamido)-1-isopropyl-5a,5b,8,
8,11a-pentamethyl-2-oxo-3,3a,4,5,5a,5b,6,7,7a,8,9,10,11,
11a,11b,12,13,13a-octadecahydro-2H-cyclopenta[a]
chrysen-9-yl)oxy)carbonyl)-2,2-dimethylcyclobutane-1-
carboxylic acid,
(1R,3S)-3-((((3aR,5aR,5bR,7aR,9S,11aR,11bR,13aS)-3a-
(2-(3-(4-chlorophenyl)-1-(ethoxycarbonyl)-1H-pyrazole-
5-carboxamido)-2-methylpropanamido)-1-isopropyl-5a,
5b,8,8,11a-pentamethyl-2-oxo-3,3a,4,5,5a,5b,6,7,7a,8,9,
10,11,11a,11b,12,13,13a-octadecahydro-2H-cyclopenta
[a]chrysen-9-yl)oxy)carbonyl)-2,2-dimethylcyclobutane-
1-carboxylic acid,
(1R,3S)-3-((((3aR,5aR,5bR,7aR,9S,11aR,11bR,13aS)-3a-
(2-(1-(ethoxycarbonyl)-3-(4-fluorophenyl)-1H-pyrazole-
5-carboxamido)-2-methylpropanamido)-1-isopropyl-5a,
5b,8,8,11a-pentamethyl-2-oxo-3,3a,4,5,5a,5b,6,7,7a,8,9,
10,11,11a,11b,12,13,13a-octadecahydro-2H-cyclopenta
[a]chrysen-9-yl)oxy)carbonyl)-2,2-dimethylcyclobutane-
1-carboxylic acid,
(1R,3S)-3-((((3aR,5aR,5bR,7aR,9S,11aR,11bR,13aS)-1-
isopropyl-5a,5b,8,8,11a-pentamethyl-3a-(2-methyl-2-(3-
(4-(trifluoromethyl)phenyl)-1H-pyrazole-5-carbox-
amido)propanamido)-2-oxo-3,3a,4,5,5a,5b,6,7,7a,8,9,10,
11,11a,11b,12,13,13a-octadecahydro-2H-cyclopenta[a]
chrysen-9-yl)oxy)carbonyl)-2,2-dimethylcyclobutane-1-
carboxylic acid,
(1R,3S)-3-((((3aR,5aR,5bR,7aR,9S,11aR,11bR,13aS)-3a-
(2-(1-(ethoxycarbonyl)-3-(4-(trifluoromethyl)phenyl)-
1H-pyrazole-5-carboxamido)-2-methylpropanamido)-1-
isopropyl-5a,5b,8,8,11a-pentamethyl-2-oxo-3,3a,4,5,5a,
5b,6,7,7a,8,9,10,11,11a,11b,12,13,13a-octadecahydro-
2H-cyclopenta[a]chrysen-9-yl)oxy)carbonyl)-2,2-
dimethylcyclobutane-1-carboxylic acid,
(1R,3S)-3-((((3aR,5aR,5bR,7aR,9S,11aR,11bR,13aS)-3a-
(2-(3-(4-chlorophenyl)-1-((2-(2-methoxyethoxy)ethoxy)
carbonyl)-1H-pyrazole-5-carboxamido)-2-methylpro-
panamido)-1-isopropyl-5a,5b,8,8,11a-pentamethyl-2-
oxo-3,3a,4,5,5a,5b,6,7,7a,8,9,10,11,11a,11b,12,13,13a-
octadecahydro-2H-cyclopenta[a]chrysen-9-yl)oxy)
carbonyl)-2,2-dimethylcyclobutane-1-carboxylic acid,
(1R,3S)-3-((((3aR,5aR,5bR,7aR,9S,11aR,11bR,13aS)-3a-
(2-(3-(4-chlorophenyl)-1-(2,5,8,11-tetraoxadodecanoyl)-
1H-pyrazole-5-carboxamido)-2-methylpropanamido)-1-
isopropyl-5a,5b,8,8,11a-pentamethyl-2-oxo-3,3a,4,5,5a,
5b,6,7,7a,8,9,10,11,11a,11b,12,13,13a-octadecahydro-
2H-cyclopenta[a]chrysen-9-yl)oxy)carbonyl)-2,2-
dimethylcyclobutane-1-carboxylic acid,
(1R,3S)-3-((((3aR,5aR,5bR,7aR,9S,11aR,11bR,13aS)-3a-
(2-(3-(4-chlorophenyl)-1-(((dimethoxyphosphoryl)oxy)
methyl)-1H-pyrazole-5-carboxamido)-2-methylpropana-
mido)-1-isopropyl-5a,5b,8,8,11a-pentamethyl-2-oxo-3,
3a,4,5,5a,5b,6,7,7a,8,9,10,11,11a,11b,12,13,13a-
octadecahydro-2H-cyclopenta[a]chrysen-9-yl)oxy)
carbonyl)-2,2-dimethylcyclobutane-1-carboxylic acid,
(1R,3S)-3-((((3aR,5aR,5bR,7aR,9S,11aR,11bR,13aS)-3a-
(2-(3-(4-chlorophenyl)-1-((phosphonooxy)methyl)-1H-
pyrazole-5-carboxamido)-2-methylpropanamido)-1-iso-
propyl-5a,5b,8,8,11a-pentamethyl-2-oxo-3,3a,4,5,5a,5b,
6,7,7a,8,9,10,11,11a,11b,12,13,13a-octadecahydro-2H-
cyclopenta[a]chrysen-9-yl)oxy)carbonyl)-2,2-
dimethylcyclobutane-1-carboxylic acid,
(1R,3S)-3-((((3aR,5aR,5bR,7aR,9S,11aR,11bR,13aS)-1-
isopropyl-5a,5b,8,8,11a-pentamethyl-2-oxo-3a-(1-(3-
phenyl-1H-pyrazole-5-carboxamido)cyclopropane-1-car-
boxamido)-3,3a,4,5,5a,5b,6,7,7a,8,9,10,11,11a,11b,12,
13,13a-octadecahydro-2H-cyclopenta[a]chrysen-9-yl)
oxy)carbonyl)-2,2-dimethylcyclobutane-1-carboxylic
acid,
(1S,3R)-3-((((3aR,5aR,5bR,7aR,9S,11aR,11bR,13aS)-1-
isopropyl-5a,5b,8,8,11a-pentamethyl-2-oxo-3a-(1-(3-
phenyl-1H-pyrazole-5-carboxamido)cyclopropane-1-car-
boxamido)-3,3a,4,5,5a,5b,6,7,7a,8,9,10,11,11a,11b,12,
13,13a-octadecahydro-2H-cyclopenta[a]chrysen-9-yl)
oxy)carbonyl)-2,2-dimethylcyclobutane-1-carboxylic
acid,
(1R,3S)-3-((((3aR,5aR,5bR,7aR,9S,11aR,11bR,13aS)-1-
isopropyl-3a-(1-(1-(methoxycarbonyl)-3-phenyl-1H-
pyrazole-5-carboxamido)cyclopropane-1-carboxamido)-
5a,5b,8,8,11a-pentamethyl-2-oxo-3,3a,4,5,5a,5b,6,7,7a,8,
9,10,11,11a,11b,12,13,13a-octadecahydro-2H-cyclopenta
[a]chrysen-9-yl)oxy)carbonyl)-2,2-dimethylcyclobutane-
1-carboxylic acid,
(1R,3S)-3-((((3aR,5aR,5bR,7aR,9S,11aR,11bR,13aS)-3a-
(1-(1-(ethoxycarbonyl)-3-phenyl-1H-pyrazole-5-carbox-
amido)cyclopropane-1-carboxamido)-1-isopropyl-5a,5b,
8,8,11a-pentamethyl-2-oxo-3,3a,4,5,5a,5b,6,7,7a,8,9,10,
11,11a,11b,12,13,13a-octadecahydro-2H-cyclopenta[a]
chrysen-9-yl)oxy)carbonyl)-2,2-dimethylcyclobutane-1-
carboxylic acid,
(1R,3S)-3-((((3aR,5aR,5bR,7aR,9S,11aR,11bR,13aS)-3a-
(1-(1-(ethoxycarbonyl)-3-(p-tolyl)-1H-pyrazole-5-car-
boxamido)cyclopropane-1-carboxamido)-1-isopropyl-5a,
5b,8,8,11a-pentamethyl-2-oxo-3,3a,4,5,5a,5b,6,7,7a,8,9,
10,11,11a,11b,12,13,13a-octadecahydro-2H-cyclopenta
[a]chrysen-9-yl)oxy)carbonyl)-2,2-dimethylcyclobutane-
1-carboxylic acid,
(1R,3S)-3-((((3aR,5aR,5bR,7aR,9S,11aR,11bR,13aS)-3a-
(1-(3-(4-chlorophenyl)-1-(ethoxycarbonyl)-1H-pyrazole-
5-carboxamido)cyclopropane-1-carboxamido)-1-isopro-
pyl-5a,5b,8,8,11a-pentamethyl-2-oxo-3,3a,4,5,5a,5b,6,7,
7a,8,9,10,11,11a,11b,12,13,13a-octadecahydro-2H-
cyclopenta[a]chrysen-9-yl)oxy)carbonyl)-2,2-
dimethylcyclobutane-1-carboxylic acid,
(1R,3S)-3-((((3aR,5aR,5bR,7aR,9S,11aR,11bR,13aS)-3a-
(1-(1-(ethoxycarbonyl)-3-(4-fluorophenyl)-1H-pyrazole-
5-carboxamido)cyclopropane-1-carboxamido)-1-isopro-
pyl-5a,5b,8,8,11a-pentamethyl-2-oxo-3,3a,4,5,5a,5b,6,7,
7a,8,9,10,11,11a,11b,12,13,13a-octadecahydro-2H-
cyclopenta[a]chrysen-9-yl)oxy)carbonyl)-2,2-
dimethylcyclobutane-1-carboxylic acid,
(1R,3S)-3-((((3aR,5aR,5bR,7aR,9S,11aR,11bR,13aS)-1-
isopropyl-5a,5b,8,8,11a-pentamethyl-2-oxo-3a-(1-(3-(4-
(trifluoromethyl)phenyl)-1H-pyrazole-5-carboxamido)
cyclopropane-1-carboxamido)-3,3a,4,5,5a,5b,6,7,7a,8,9,
10,11,11a,11b,12,13,13a-octadecahydro-2H-cyclopenta
[a]chrysen-9-yl)oxy)carbonyl)-2,2-dimethylcyclobutane-
1-carboxylic acid,
(1R,3S)-3-((((3aR,5aR,5bR,7aR,9S,11aR,11bR,13aS)-3a-
(1-(1-(ethoxycarbonyl)-3-(4-(trifluoromethyl)phenyl)-
1H-pyrazole-5-carboxamido)cyclopropane-1-carbox-
amido)-1-isopropyl-5a,5b,8,8,11a-pentamethyl-2-oxo-3,
3a,4,5,5a,5b,6,7,7a,8,9,10,11,11a,11b,12,13,13a-
octadecahydro-2H-cyclopenta[a]chrysen-9-yl)oxy)
carbonyl)-2,2-dimethylcyclobutane-1-carboxylic acid,
(1R,3S)-3-((((3aR,5aR,5bR,7aR,9S,11aR,11bR,13aS)-3a-
(1-(3-(4-chlorophenyl)-1-((2-(2-methoxyethoxy)ethoxy)

carbonyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-(2,5,8,11-tetraoxadodecanoyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-(((dimethoxyphosphoryl)oxy)methyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-((phosphonooxy)methyl)-1H-pyrazole-5-carboxamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(3-phenyl-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(1-(3-phenyl-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-(1-(1-(methoxycarbonyl)-3-phenyl-1H-pyrazole-5-carboxamido)cyclobutane-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-phenyl-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-(p-tolyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-(ethoxycarbonyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-(4-fluorophenyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(1-(3-(4-(trifluoromethyl)phenyl)-1H-pyrazole-5-carboxamido)cyclobutane-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(1-(ethoxycarbonyl)-3-(4-(trifluoromethyl)phenyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-((2-(2-methoxyethoxy)ethoxy)carbonyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-(2,5,8,11-tetraoxadodecanoyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-(((dimethoxyphosphoryl)oxy)methyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(1-(3-(4-chlorophenyl)-1-((phosphonooxy)methyl)-1H-pyrazole-5-carboxamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(3-(3-phenyl-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(3-(3-phenyl-1H-pyrazole-5-carboxamido)azetidine-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(ethoxycarbonyl)-3-phenyl-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(ethoxycarbonyl)-3-(4-fluorophenyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(3-(4-chlorophenyl)-1-(ethoxycarbonyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(ethoxycarbonyl)-3-(4-(trifluoromethyl)phenyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(3-(4-chlorophenyl)-1-(((dimethoxyphosphoryl)oxy)methyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(3-(4-chlorophenyl)-1-((phosphonooxy)methyl)-1H-pyrazole-5-carboxamido)azetidine-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(3-(3-phenyl-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-1-isopropyl-5a,5b,8,8,11a-pentamethyl-2-oxo-3a-(3-(3-phenyl-1H-pyrazole-5-carboxamido)oxetane-3-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(ethoxycarbonyl)-3-phenyl-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(ethoxycarbonyl)-3-(4-fluorophenyl)-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(3-(4-chlorophenyl)-1-(ethoxycarbonyl)-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, and (1R,3S)-3-((((3aR,5aR,5bR,7aR,9S,11aR,11bR,13aS)-3a-(3-(3-(4-chlorophenyl)-1-((phosphonooxy)methyl)-1H-pyrazole-5-carboxamido)oxetane-3-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, or pharmaceutically acceptable salts and prodrugs of compounds are also contemplated.

The absolute configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 5%, in particularly less than 2% or 1% of the other isomers. Thus when a compound of formula (I) is for instance specified as (R), this means that the compound is substantially free of (S) isomer; when the compound of formula (I) is for instance specified as E, this means that the compound is free of the Z isomer; when the compound of formula (I) is for instance specified as cis isomer, this means that the compound is free of the trans isomer.

The present invention also provides a pharmaceutical composition that includes at least one compound of formula (I) as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cure that infection, specifically in the form of a pharmaceutical composition.

Also provided herein are processes for preparing compounds of formula (I) described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or a retroviral infection genetically related to AIDS.

Anti HIV inhibitory potential of the compounds of present invention may be demonstrated by any one or more methodologies known in the art, such as by using the assays described in Mossman T, December 1983, Journal of immunological methods, 65 (1-2), 55-63 and SPC Cole, cancer chemotherapy and Pharmacology, 1986, 17, 259-263.

DETAILED DESCRIPTION OF THE INVENTION

The present invention provides novel triterpenone derivatives and related compounds, which may be used as antiviral particularly as anti-HIV compounds and processes for the synthesis of these compounds and their pharmaceutically acceptable salts thereof, together with pharmaceutically acceptable carriers, excipients or diluents, which can be used for the treatment of diseases, condition and/or disorders mediated by viral infections, are also provided.

The following definitions apply to the terms as used herein:

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond, e.g., methyloxy, ethyloxy, n-propyloxy, 1-methylethyloxy (isopropyloxy), n-butyloxy, n-pentyloxy, 1,1-dimethylethyloxy (t-butyloxy),

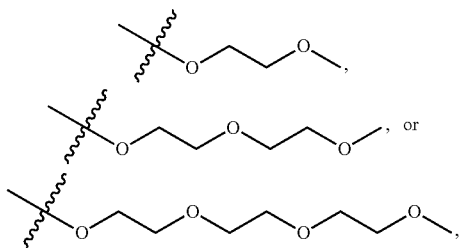

The term "amine" refers to an organic compounds and functional groups that contain a basic nitrogen atom with a lone pair. Amines are derivatives of ammonia, wherein one or more hydrogen atoms have been replaced by a substituent such as an alkyl or aryl group these may respectively be called alkylamines and arylamines; amines in which both types of substituent are attached to one nitrogen atom may be called alkylarylamines. Important amines include amino acids, trimethylamine, and aniline.

The term "aminoalkyl" refers to any amino derivative of an alkyl radical more specifically dimethylamino.

The term "alkylamino" refers to an amino substituent which is further substituted with one or two alkyl groups.

The term "alkylaminoalkyl" refers to an alkyl radical, as defined herein, substituted with an alkylamine, as defined herein.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapthylethyl, adamantyl and norbornyl groups, bridged cyclic groups and spirobicyclic groups, e.g., spiro (4,4) non-2-yl.

The term "aryl" refers to an aromatic radical having from 6 to 14 carbon atoms such as phenyl, naphthyl, tetrahydronapthyl, indanyl, and biphenyl.

The term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluoro chloromethyl, dichloro fluoromethyl, difluoroethyl, difluoropropyl and the like.

The terms "halogen" or "halo" includes fluorine, chlorine, bromine, or iodine.

The term "hydroxyl" refers to —OH.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl and 1,4-Thiazine-1,1-dione. The heterocyclic ring radical may be attached to the main structure at any heteroatom or carbon atom that results in the creation of a stable structure.

The term "heteroaryl" refers to an aromatic heterocyclic ring radical. Examples of such heteroaryl include, but are not limited to pyridyl, pyrazinyl, furanyl, quinolinyl, tetrazoyl, triazolyl, 1,3-Diaza-1H-indenyl, thiazolyl, imidazolyl, pyrazolyl, isoxazolyl, pyrazolo[1,5-a]pyrimidinyl, 1,3,4-oxadiazolyl, thiazolidinyl, isothiazolyl, quinuclidinyl, isothiazolidinyl, indolyl, isoindolyl, indolinyl and isoindolinyl. The heteroaryl ring radical may be attached to the main structure at any heteroatom or carbon atom that results in the creation of a stable structure.

The term "hydroxyalkyl" means a linear monovalent hydrocarbon radical of one to six carbon atoms or a branched monovalent hydrocarbon radical of three to six carbons substituted with one or two hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl.

The term "optionally substituted" refers to replacement of one or more hydrogen radicals in a given structure with a radical of a specified substituent including, but are not limited to: hydroxy, halo, carboxyl, cyano (CN), nitro, oxo (=O), thio (=S), alkyl, methyl sulfonyl, haloalkyl, alkoxy, alkenyl, aryl, aralkyl, cycloalkyl, cycloalkylalkyl, amino, —C(O)O-alkyl, heterocyclyl, heteroaryl, heterocyclylalkyl, heteroarylalkyl, alkylthio, arylthio, aryloxy, amino carbonyl, alkoxycarbonyl, alkylamino, arylamino, acyl, carboxylic acid, sulfonic acid, sulfonyl, phosphonic acid, and aliphatic. It is understood that the substituent may be further substituted.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:
(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;
(2) inhibiting the state, disease, disorder or condition, i.e., arresting or reducing the development of the state, disease, disorder or condition or at least one clinical or subclinical symptom thereof; or
(3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereoisomeric forms (e.g., diastereomers, enantiomers, racemates, and combinations thereof). With respect to the overall compounds described by the formula (I), the present invention extends to these stereo isomeric forms and to mixtures thereof. To the extent prior art teaches synthesis or separation of particular stereoisomers, the different stereo isomeric forms of the present invention may be separated from one another by the methods known in the art, or a given isomer may be obtained by stereospecific or asymmetric synthesis. Tautomeric forms and mixtures of compounds described herein are also contemplated.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be in conventional forms, for example, capsules, tablets, solutions, suspensions, injectables or products for topical application. Further, the pharmaceutical composition of the present invention may be formulated so as to provide desired release profile.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tableting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining. Cells ($5\times10^3$ cells/well) will be incubated in 96 well plates in the presence or absence of compounds. At the end of treatment, 20 µl of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1\times10^6$ Sup-T1 cells with 100% cell viability will be seeded in RPMI 1640, 0.1% FBS four 12 well plates. Increasing concentrations of Epap-1 peptides will be added to the cells and will be infected with HIV1$_{93\ IN\ 101}$ each at final concentration of virus equivalent to 2 ng of p24 per ml. The infected cells will be incubated at 37° C. and 5% $CO_2$ incubator for 2 hours. After 2 hours the cells will be pelleted at 350 g for 10 minutes, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hour at 37° C. The reporter expression will be quantified at appropriate time calculated inhibitory doses referrers to the concentration of these agents in this preincubation mixture.

Other relevant references useful for screening antiviral HIV activity are: Averett, D. R.1989. Anti-HIV compound assessment by two novel high capacity assays. J. Virol. Methods 23: 263-276; Schwartz, O., et al. 1998; A rapid and simple colorimeric test for the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7):1590-1603; H. Mitsuya and S. Border, Inhibition of the in vitro infectivity and cytopathic effect of human T-lymphotropic virus type lymphadenopathy-associated virus (HLTV-III/LAV) by 2,3'-dideoxynucleosides, Proc. Natl. Acad. Sci. USA, 83, 1911-15(1986); Pennington et al., Peptides 1990; Meek T. D et al., Inhibition of HIV-1 protease in infected T-limphocytes by synthetic peptide analogues, Nature, 343, p90 (1990); Weislow et al., J. Natl. Cancer Inst. 81, 577-586, 1989; T. Mimoto et al., J. Med. Chem., 42, 1789-1802, 1999; Uckun et al 1998, Antimicrobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263, Antiviral methods and protocols (Eds: D Kinchington and R. F. Schinazi) Humana Press Inc., 2000, HIV protocols (Eds: N. L. Michael and J. H. Kim) Humana Press Inc, 1999, DAIDS Virology manual from HIV laboratories, Publication NIH-97-3838, 1997, 4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01//07646, WO 01/65957, or WO 03/037908; US publication Nos. U.S. Pat. No. 4,598,095 or US 2002/

0068757; EP publication Nos. EP 0989862 or EP 0724650; *Bioorganic & Medicinal Chemistry Letters,* 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV infection, HCV infection, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme 1. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulin. Key intermediates required for synthesizing analogues are either commercially available, or can be prepared by the methods published in the literature. For example, the key intermediates in the present invention were prepared by modifying the procedures published in *Journal of organic chemistry* 2010, 75, 1285-1288; *Journal of organic chemistry* 2000, 65, 3934-3940; *Tetrahedron: asymmetry* 2008, 19, 302-308; or *Tetrahedron: asymmetry* 2003, 14, 217-223.

Another embodiment of the present invention provides process for preparation of the compounds of general formula (I) are set forth in the below generalized scheme. One of skilled in the art will recognize that below generalised scheme can be adapted to produce the compounds of general formula (I) and pharmaceutically acceptable salts according to the present invention. Wherein all symbols/variables are as defined earlier unless otherwise stated.

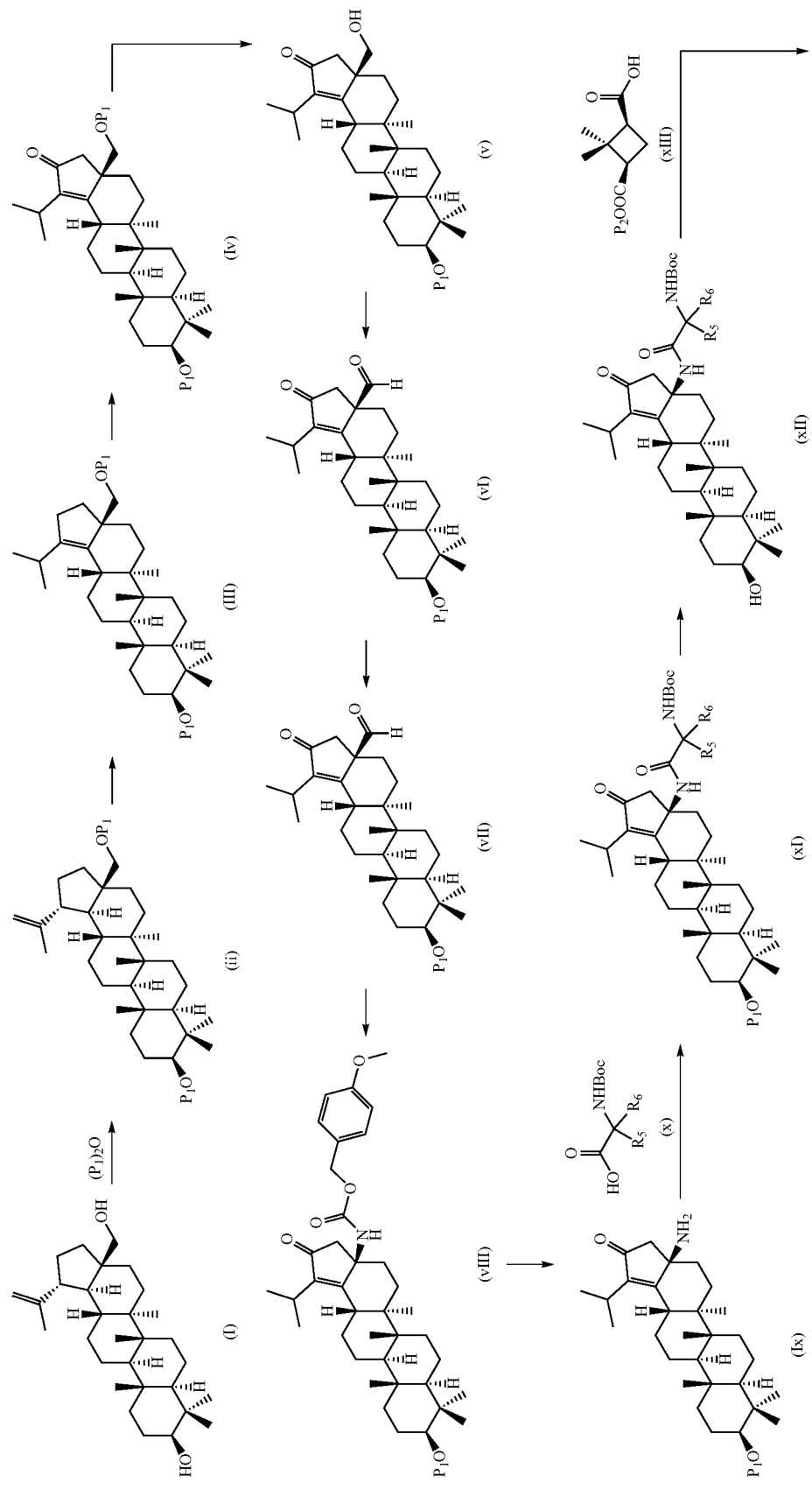
Scheme-1

-continued
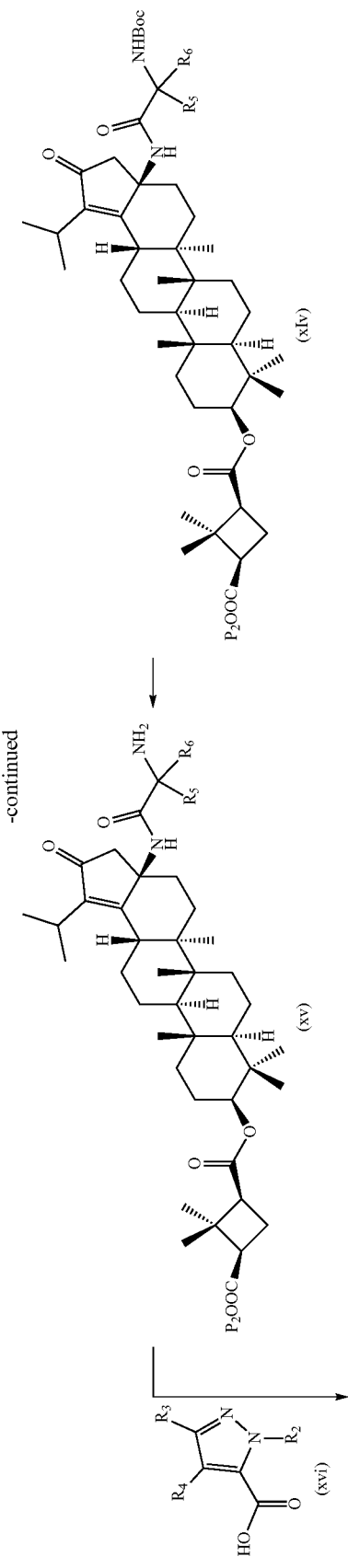
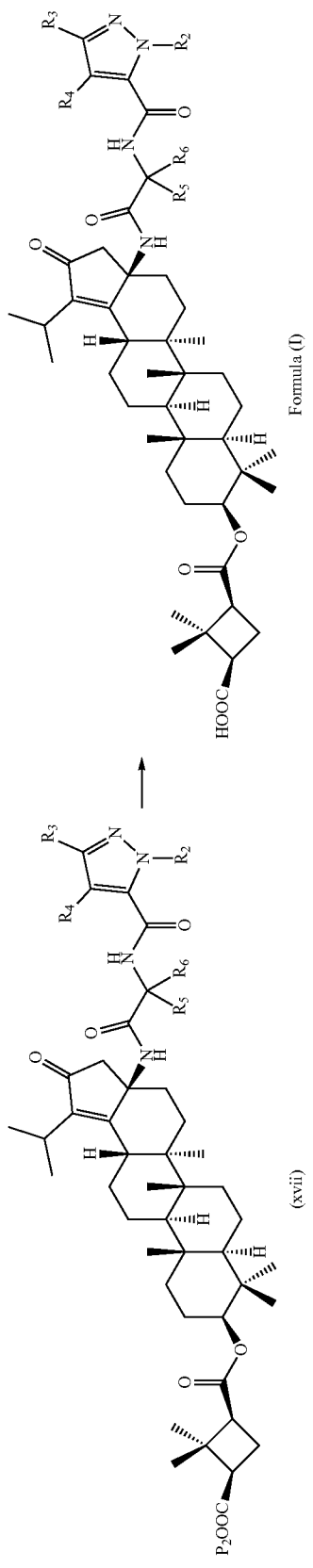
wherein R₁ = HOOC

The compounds of formula I (wherein, $R_2$, $R_3$, $R_4$, $R_5$ and $R_6$ are same as defined above) can be prepared as described in Scheme 1. The C-3 & C-28 di hydroxy compounds of formula (i) can be reacted with a suitable acetate forming reagents such as anhydrides, acid halides, mixed anhydrides or the like in the presence of bases such as triethylamine (TEA) or diisopropylethylamine (DIPEA) or pyridine or the like in the solvents such as dichloromethane (DCM), chloroform ($CHCl_3$), toluene, tetrahydrofuran (THF) or the like with or without addition of catalysts such as dimethyl amino pyridine (DMAP) or the like to give the C-3 & C-28 dihydroxy protected compounds of formula (ii) ($P_1$ and $P_2$ are protecting groups such as acetyl, benzyl or the like). The C-3 & C-28 dihydroxy protected compounds of formula (ii) can be converted to the compounds of formula (iii) in the presence of hydrogen bromide (HBr) in acetic acid (AcOH), acetic acid (AcOH) and acetic anhydride ($Ac_2O$) in solvents like toluene, benzene, xylene or the like. The compounds of formula (iii) can be converted to the compounds of formula (iv) in the presence of sodium dichromate ($Na_2Cr_2O_7$), sodium acetate (NaOAc), acetic acid (AcOH), acetic anhydride ($Ac_2O$) in solvents like toluene, benzene or the like. The C-28 hydroxy protected compounds of formula (iv) can be deprotected to give the C-28 hydroxyl compounds of formula (v) in the presence of potassium hydroxide (KOH) or the like in the combination of solvents such as toluene: ethanol (EtOH) (1:1) or with reagents like Aluminum isopropoxide (Al(i-Pro)$_3$) in solvents like 2-propanol or the like. The C-28 hydroxyl compounds of formula (v) can be converted to the C-28 aldehyde compounds of formula (vi) in the presence of pyridinium chlorochromate (PCC) or pyridinium dichromate (PDC) or Dess-martin periodinane (DMP) or Swern oxidation conditions in the solvents such as dichloromethane (DCM) or the like. The C-28 aldehyde compounds of formula (vi) can be converted to the C-28 acid compounds of formula (vii) in the presence of oxidizing agents such as sodium chlorite ($NaClO_2$) or the like in the presence of a scavenger such as 2-methyl-2-butene or the like in the presence of a buffer reagent such as sodiumdihydrogen phosphate ($NaH_2PO_4$) or the like in the combination of solvents such as tert-butanol (t-BuOH), tetrahydrofuran (THF) and water ($H_2O$) or the like. (or) The C-28 hydroxyl compounds of formula (v) can be converted in one pot method to C-28 acid compounds of formula (vii) in the presence of oxidizing agents such as 2,2,6,6-Tetramethyl-1-piperidinyloxy, free radical, 2,2,6,6-Tetramethylpiperidine 1-oxyl (TEMPO), Sodium hypochlorite (NaOCl) and Sodium chlorite ($NaClO_2$) in the presence of buffer reagent such as sodiumdihydrogen phosphate ($NaH_2PO_4$) and the base like $NaHCO_3$ in the combination of solvents like Tetrahydrofuran (THF) and water ($H_2O$). The C-28 acid compounds of formula (vii) can be converted to the C-17 carbamate compounds of formula (viii) by using the reagents like diphenylphosphoryl azide (DPPA) or ethylchloroformate and sodium azide ($NaN_3$) or the like with 4-methoxybenzyl alcohol (PMBOH), in the presence of bases such as triethylamine (TEA), or N,N-Diisopropylethylamine (DIPEA) or the like in solvents such as 1,2-DCE or THF or Toluene or the like. The C-17 carbamate compounds of formula (viii) can be deprotected in the presence of acid medium such as trifluoroacetic acid (TFA), (or) HCl/1,4-dioxane or the like in the solvents such as dichloromethane (DCM) or chloroform ($CHCl_3$) or the like to give the C-17 amine compounds of formula (ix). The C-17 amine compounds of formula (ix) can be coupled with the acid compounds of formula (x) in the presence of coupling reagents such as O-(7-Azabenzotriazol-1-yl)-N,N,N', N'-tetramethyluroniumhexafluorophosphate (HATU) (or) O-(Benzotriazol-1-yl)-N,N,N', N'-tetramethyluroniumhexafluoro phosphate (HBTU) (or) combination of 1-Ethyl-3-(3-dimethylaminopropyl)carbodiimide hydrochloride (EDC.HCl), 1-Hydroxybenzotriazole (HOBt) or the like in the presence of bases such as triethylamine (TEA) or N,N-Diisopropylethylamine (DIPEA) or the like in the solvents such as 1,2-dichloroethane (1,2-DCE), N,N-dimethylformamide (DMF) or the like to give the C-17 amide compounds of formula (xi). The C-3 protected compounds of formula (xi) can be deprotected to give the C-3 hydroxyl compounds of formula (xii) in the presence of inorganic bases such as Lithium hydroxide (LiOH) or sodium hydroxide (NaOH), or potassium hydroxide (KOH) or the like in the solvents such as methanol (MeOH):tetrahydrofuran (THF):water ($H_2O$) (4:2:1) (or) 1,4-dioxane:water ($H_2O$) (4:1) or the like. The C-3 hydroxyl compounds of formula (xii) can be coupled with the acid compounds of formula (xiii) to give the C-3 ester compounds of formula (xiv) in different ways like (a) Acid and hydroxyl group coupling in the presence of coupling reagents such as 2,4,6-trichlorobenzyl chloride, or the like in the presence of bases such as triethylamine (TEA) or N,N-Diisopropylethylamine (DIPEA) and catalysts such as 4-dimethylaminopyridine (DMAP) in the solvents such as 1,2-dichloroethane (1,2-DCE), dichloromethane (DCM) or the like.

(b) Acid and hydroxyl group coupling in the presence of coupling reagents such as EDCI, HOBt in the presence of bases such as triethylamine (TEA), or N,N-Diisopropylethylamine (DIPEA) and catalysts such as 4-dimethylaminopyridine (DMAP) in the solvents such as dichloromethane (DCM) and N,N-dimethylformamide (DMF) or the like.

The C-17 substituted N-Boc protected compounds of formula (xiv) can be deprotected with reagent like trifluoroacetic acid (TFA) or HCl/1,4-dioxane or the like in the solvents such as dichloromethane (DCM) or the like to give the C-17 substituted amine compounds of formula (xv). The C-17 substituted amine compounds of formula (xv) can be coupled with the compounds of formula (xvi) to give the compounds of formula (xvii) in different ways like a) acid and amine coupling in the presence of coupling reagents such as 1-Ethyl-3-(3-dimethylaminopropyl) carbodiimide hydrochloride (EDC.HCl), 1-Hydroxybenzotriazole (HOBt), and catalyst such as 4-Dimethylaminopyridine (DMAP) or the like in the presence of bases such as triethylamine (TEA) or N,N-Diisopropylethylamine (DIPEA) or the like in the solvents such as 1,2-dichloroethane (1,2-DCE) or N,N-dimethylformamide (DMF) or the like.

The ester compounds of formula (xvii) can be hydrolyzed to give the acid compounds of formula 1 in the presence of aqueous solution of inorganic bases such as Lithium hydroxide (LiOH) or sodium hydroxide (NaOH) or potassium hydroxide (KOH) or the like in the combination of solvents such as tetrahydrofuran (THF):methanol (MeOH) (1:1) or the like.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I. Particular isotopes are —CD$_3$ or —C(D$_2$)-. Isotopically labeled compounds of the present inventions can generally be prepared by following procedures analogous to those disclosed in the Schemes and/or in the Examples herein below, by substituting an isotopically labeled reagent for a non-isotopically labeled reagent.

Abbreviations: The abbreviations used in the entire specification may be summarized herein below with their particular meaning: $^1$H NMR (Proton Nuclear Magnetic Resonance); Hz (hertz); MHz (megahertz); CDCl$_3$ (Deuterated Chloroform); DMSO (Dimethylsulfoxide); δ (delta); ppm (parts per million); s (singlet); d (doublet); dd (doublet of doublet(s)); m (multiplet); J (coupling constant); J$_{AB}$ (coupling constant); ABq (AB quartet); bs (broad singlet); ml (millilitre); ° C. (degree Celsius); mol (mole(s)); mmol (millimole(s)); M (molar solution); N (Normal solution); mg (milligram(s)); g (gram(s)); pH (Pouvoir hydrogen); Pd/C (palladium on activated carbon); eq (equivalent(s)); psi (pounds per square inch); ESI-MS (Electrospray ionization mass spectrometry); m/z (mass to charge ratio); M–H$^-$ (parent mass spectrum peak minus hydrogen-); (M+H)$^+$ (parent mass spectrum peak plus hydrogen$^+$); DCM (Dichloromethane); TEA (Triethylamine); DMF (N,N-dimethylformamide); MeOH (Methanol); THF (Tetrahydrofuran); Na$_2$SO$_4$ (sodium sulfate); HCl (Hydrochloric acid); TLC (Thin Layer Chromatography); % (percentage); D-MAP (4-Dimethylaminopyridine); HOBt (Hydroxybenzotriazole); NaOH (sodium hydroxide); KOH (potassium hydroxide); EDC.HCl (1-(3-Dimethylaminopropyl)-3-ethylcarbodiimide Hydrochloride); MTBE (Methyl tert-butyl ether).

Experimental

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest one of ordinary skill in the art without departing from the spirit of the present invention. Thus, the skilled artisan will appreciate how the experiments and examples may be further implemented as disclosed by variously altering the following examples, substituents, reagents, or conditions.

EXAMPLES

Example 1: Preparation of (1R,3S)-3-(((((3aR,5aR, 5bR,7aR,9S,11aR,11bR,13aS)-1-isopropyl-5a,5b,8, 8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8,9,10,11,11a,11b,12,13, 13a-octadecahydro-2H-cyclopenta[a]chrysen-9-yl) oxy)carbonyl)-2,2-dimethylcyclobutane-1-carboxylic acid

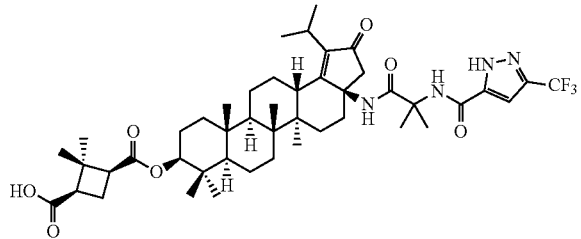

Step 1: Synthesis of 1-benzyl 3-((3aR,5aR,5bR, 7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido) propanamido)-2-oxo-3,3a,4,5,5a,5b,6,7,7a,8,9,10,11,11a,11b,12,13,13a-octadecahydro-2H-cyclopenta[a]chrysen-9-yl)(1R, 3S)-2,2-dimethylcyclobutane-1,3-dicarboxylate

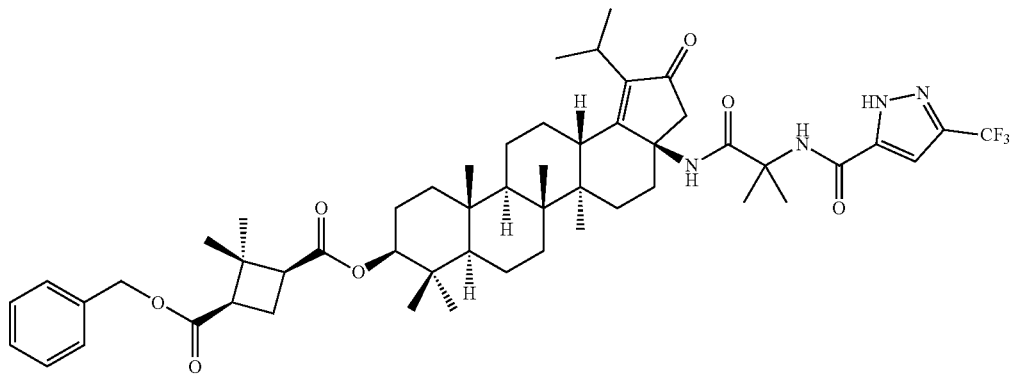

To a stirred solution of 3-(trifluoromethyl)-1H-pyrazole-5-carboxylic acid (0.92 g, 4.86 mmol, 1.5 eq) in DMF (25 mL) was added TEA (1.80 mL, 12.97 mmol, 4.0 eq), EDC HCl (1.24 g, 6.48 mmol, 2.0 eq), HOBt (0.65 g, 4.86 mmol, 1.5 eq), followed by D-MAP (0.19 g, 1.62 mmol, 0.5 eq). The reaction mixture was stirred at room temperature for about minutes, then 1-((3aR,5aR,5bR,7aR,9S,11aR,11bR,13aS)-3a-(2-amino-2-methyl propanamido)-1-isopropyl-5a,5b,8,8,11a-pentamethyl-2-oxo 3,3a,4,5,5a,5b,6,7,7a,8,9,10,11, 11a,11b,12,13,13a-octadecahydro-2H-cyclopenta[a]chrysen-9-yl) 3-benzyl (1S,3R)-2,2-dimethylcyclobutane-1,3-dicarboxylate (WO 2016/178092 A2, Intermediate 1, 2.5 g, 3.24 mmol, 1.0 eq) was added and stirred at room temperature for overnight. After completion of the reaction (monitored by TLC), the reaction mixture was diluted with ice cold water (150 mL) and stirred at room temperature for about 30 minutes. The precipitates formed were collected by filtration and were washed with water (200 mL) and dried under vacuum to obtain the solid. The resulting solid compound was purified by silica gel column chromatography by using 0-3% methanol in dichloromethane gradient. The fractions containing the expected product were combined and concentrated under reduced pressure to obtain the title compound (1.52 g, yield: 50.00%) as a white solid. $^1$H NMR (300 MHz, CDCl$_3$): δ ppm 14.3 (bs, 1H), 8.34 (s, 1H), 7.42-7.38 (m, 7H), 5.58-5.55 (d, J=9.0, 1H), 5.14-5.04 (m, 2H), 4.46 (dd, J=10.8, 3.6 Hz, 1H), 3.07 (s, 3H), 2.82-2.73 (m, 4H), 2.46-2.27 (m, 4H), 2.12-2.06 (m, 1H), 1.90-1.86 (m, 3H), 1.73-1.69 (m, 4H), 1.63-1.59 (m, 4H), 1.44-1.41 (m, 9H), 1.32-1.30 (m, 6H), 1.23-1.10 (m, 6H), 1.05-1.01 (m, 5H), 0.91-0.81 (m, 9H); ESI-MS: m/z 934.21 (M+H)$^+$.

Step 2: Synthesis of (1R,3S)-3-((((3aR,5aR,5bR,7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido) propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)(1R,3S)-2,2-dimethylcyclobutane-1,3-dicarboxylate (step 1, 1.50 g, 1.60 mmol, 1.0 eq) in MeOH (8.5 mL) and THF (8.5 mL) was added aqueous 2.5N KOH solution (4.82 mL, 11.96 mmol, 7.5 eq). The reaction mixture was stirred at room temperature for overnight. After completion of the reaction (monitored by TLC), the organic phase was evaporated under reduced pressure, the reaction mixture was diluted with water (20 mL), cooled to 0° C., pH adjusted to 5.0 with 1N HCl and extracted with DCM (3×50 mL). The combined organic extracts were washed with water (30 mL), dried over sodium sulphate, filtered and evaporated under reduced pressure. The residue was purified by silica gel column chromatography by using 0-4% methanol in dichloromethane gradient. The fractions containing the expected product were combined and concentrated under reduced pressure to obtain the solid. To this solid compound, methyl tert-butyl ether (5 mL) was added and refluxed for about 30 minutes. The mixture was cooled to room temperature; hexane (10 mL) was added, stirred at room temperature for about 2 hours. The solid was filtered, washed with MTBE:hexane (2, 10 ml) and dried under vacuum to obtain the title compound (0.45 g, yield: 33.33%) as an off-white solid. $^1$H NMR (300 MHz, CDCl$_3$): δ ppm 14.3 (bs, 1H), 12.15 (bs, 1H), 8.34 (s, 1H), 7.42-7.38 (m, 2H), 5.58-5.55 (d, J=9.0, 1H), 4.46 (dd, J=10.8, 3.6 Hz, 1H), 3.07 (s, 3H), 2.82-2.73 (m, 4H), 2.46-2.27 (m, 4H), 2.12-2.06 (m, 1H), 1.90-1.86 (m, 3H), 1.73-1.69 (m, 4H), 1.63-1.59 (m, 4H), 1.44-1.41 (m, 9H), 1.32-1.30 (m, 6H), 1.23-1.10 (m, 6H), 1.05-1.01 (m, 5H), 0.91-0.81 (m, 9H); ESI-MS: m/z 844.71 (M+H)$^+$.

Example 2: Preparation of (1R,3S)-3-((((3aR,5aR,5bR,7aR,9S,11aR,11bR,13aS)-3a-(2-(1-(ethoxycarbonyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b,6,7,7a,8,9,10,11,11a,11b, 12,13, 13a-octadecahydro-2H-cyclopenta[a]chrysen-9-yl)oxy)carbonyl)-2,2-dimethylcyclobutane-1-carboxylic acid

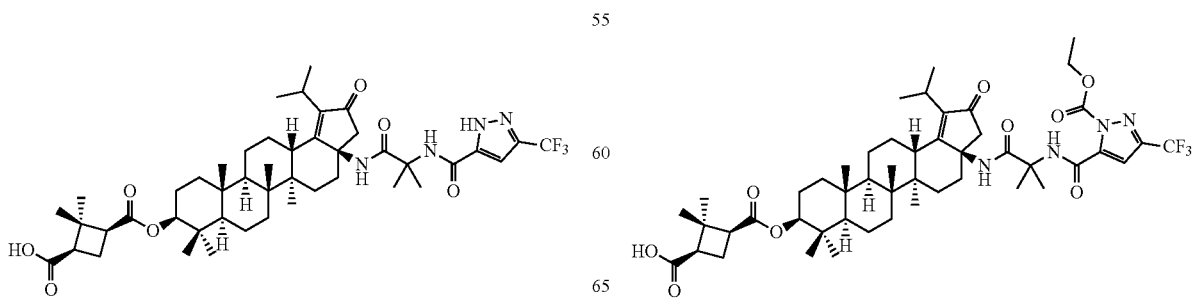

Step 1: Synthesis of 1-benzyl 3-((3aR,5aR,5bR,7aR,9S,11aR,11bR,13aS)-3a-(2-(1-(ethoxycarbonyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate

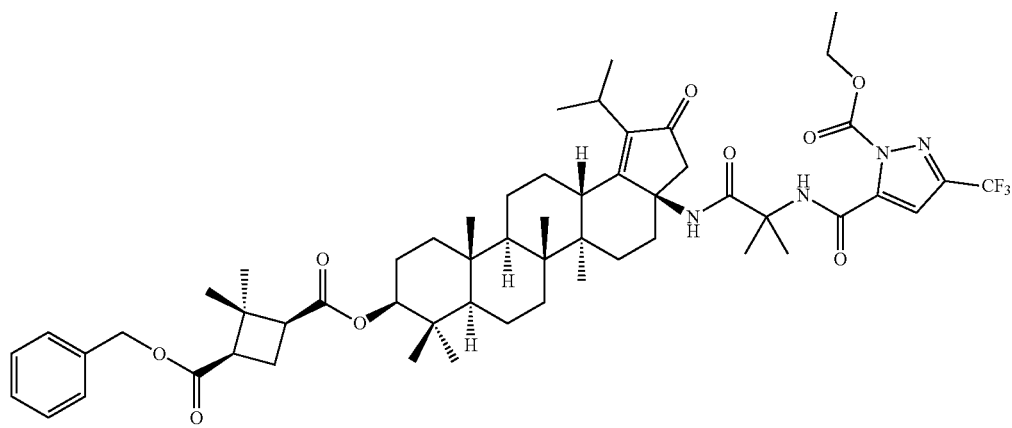

To a stirred solution of 1-benzyl 3-((3aR,5aR,5bR,7aR,9S,11aR,11bR,13aS)-1-isopropyl-5a,5b,8,8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (Example 1, step 1, 0.5 g, 0.536 mmol, 1.0 eq) in acetonitrile (10 mL) was added potassium carbonate (0.22 g, 1.60 mmol, 3.0 eq) followed by ethyl chloroformate, (0.101 mL, 1.07 mmol, 2.0 eq) was added at 0° C. and stirred at room temperature for overnight. After completion of the reaction (monitored by TLC), the reaction mixture was diluted with water (50 mL) and extracted with ethyl acetate (100 mL) followed by water and brine solution, then the organic layer was dried under anhydrous sodium sulphate, concentrated under reduced pressure. The resulting crude compound was purified by silica gel column chromatography by using 0-3% methanol in dichloromethane gradient. The fractions containing the expected product were combined and concentrated under reduced pressure to obtain the title compound (0.12 g, yield: 53.91%) as a white solid. ESI-MS: m/z 1005 (M+H)$^+$.

Step 2: Synthesis of (1R,3S)-3-((((3aR,5aR,5bR,7aR,9S,11aR,11bR,13aS)-3a-(2-(1-(ethoxycarbonyl)-3-(trifluoromethyl)-1H-pyrazole-5-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl)oxy)carbonyl)-2,2-dimethylcyclobutane-1-carboxylic acid

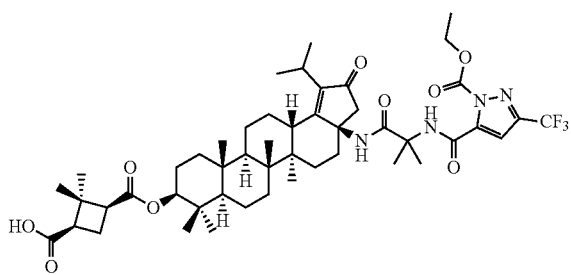

To a stirred solution of 1-benzyl 3-((3aR,5aR,5bR,7aR, 9S,11aR,11bR,13aS)-1-isopropyl-5a,5b,8,8,11a-pentamethyl-3a-(2-methyl-2-(3-(trifluoromethyl)-1H-pyrazole-5-carboxamido)propanamido)-2-oxo-3,3a,4,5,5a,5b,6,7,7a,8, 9,10,11,11a,11b,12,13,13a-octadecahydro-2H-cyclopenta[a]chrysen-9-yl)(1R,3S)-2,2-dimethylcyclobutane-1,3-dicarboxylate (step 1, 0.12 g, 0.938 mmol, 1.0 eq) in ethyl acetate (8.5 mL) and added 10% palladium on carbon (65 mg) at 50 psi hydrogen gas. The reaction mixture was stirred at room temperature for about three hours. After completion of the reaction (monitored by TLC), the reaction mass was filtered through celite pad under nitrogen atmosphere. Then the filtrate was evaporated under reduced pressure pale yellow solid was obtained, then the crude compound was purified by silica gel column chromatography by using 0-4% methanol in dichloromethane gradient. The fractions containing the expected product were combined and concentrated under reduced pressure to obtain the solid. To this solid compound, methyl tert-butyl ether (5 mL) was added and refluxed for about 30 minutes. The mixture was cooled to room temperature then hexane (10 mL) was added and stirred at room temperature for about 2 hours. The solid was filtered, washed with MTBE:hexane (2, 10 ml) and dried under vacuum to obtain the title compound (20 mg, yield: 20.00%) as an off-white solid. ESI-MS: m/z 915 (M+H)⁺.

Example 3: Preparation of (1R,3S)-3-(((((3aR,5aR, 5bR,7aR,9S,11aR,11bR,13aS)-1-isopropyl-5a,5b,8, 8,11a-pentamethyl-3a-(2-methyl-2-(3-phenyl-1H-pyrazole-5-carboxamido) propanamido)-2-oxo-3,3a, 4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

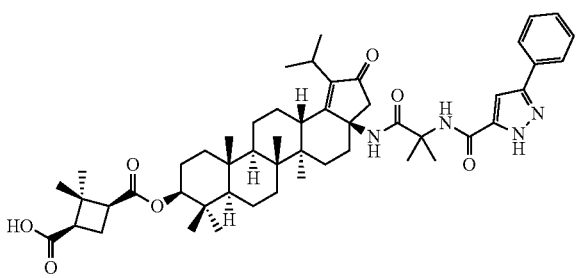

Step 1: Synthesis of 1-benzyl 3-((3aR,5aR,5bR, 7aR,9S,11aR,11bR,13aS)-1-isopropyl-5a,5b,8,8,11a-pentamethyl-3a-(2-methyl-2-(3-phenyl-1H-pyrazole-5-carboxamido) propanamido)-2-oxo-3,3a,4,5,5a,5b, 6,7,7a,8,9,10,11,11a,11b,12,13,13a-octadecahydro-2H-cyclopenta[a]chrysen-9-yl)(1R,3S)-2,2-dimethylcyclobutane-1,3-dicarboxylate

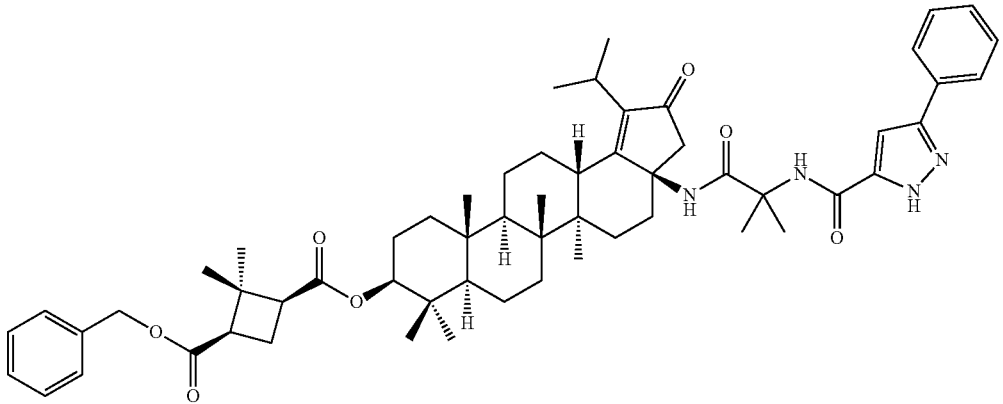

To a stirred solution of 5phenyl-2H-pyrazole-3-carboxylic acid (0.91 g, 4.86 mmol, 1.5 eq) in DMF (25 mL) was added TEA (1.80 ml, 12.97 mmol, 4.0 eq), EDC.HCl (1.24 g, 6.48 mmol, 2.0 eq), HOBt (0.65 g, 4.86 mmol, 1.5 eq), followed by DMAP (0.19 g, 1.62 mmol, 0.5 eq). The reaction mixture was stirred at room temperature for about 30 minutes, then 1-((3aR,5aR,5bR,7aR,9S,11aR,11bR, 13aS)-3a-(2-amino-2-methylpropanamido)-1-isopropyl-5a, 5b,8,8,11a-pentamethyl-2-oxo-3,3a,4,5,5a,5b,6,7,7a,8,9,10, 11,11a,11b,12,13, 13a-octadecahydro-2H-cyclopenta[a] chrysen-9-yl) 3-benzyl (1S,3R)-2,2-dimethyl cyclobutane-1,3-dicarboxylate (WO 2016/178092 A2, Intermediate 1, 2.5 g, 3.24 mmol, 1.0 eq) was added and stirred at room temperature for overnight. After completion of the reaction (monitored by TLC), the reaction mixture was diluted with ice cold water (150 mL) and stirred at room temperature for 30 minutes. The precipitates formed were collected by filtration and were washed with water (200 mL) and dried under vacuum to obtain the solid. The resulting solid compound was purified by silica gel column chromatography by using 0-3% methanol in dichloromethane gradient. The fractions containing the expected product were combined and concentrated under reduced pressure to obtain the title compound (1.4 g, yield: 45.90%) as a white solid. $^1$H NMR (300 MHz, CDCl$_3$): δ ppm 13.6 (bs, 1H), 7.97 (s, 1H), 7.79-7.77 (m, 2H), 7.71-7.67 (m, 1H), 7.56 (bs, 1H), 7.46-7.32 (m, 8H), 5.12-5.06 (d, ABq, J$_{AB}$=12.3 Hz, 2H), 4.46 (dd, J=10.8, 3.6 Hz, 1H), 4.14-4.12 (m, 1H), 3.13-3.08 (m, 1H), 3.00-2.80 (m, 4H), 2.34 (m, 4H), 1.98-1.86 (m, 5H), 1.52 (m, 9H), 1.37-1.23 (m, 12H), 1.15-1.12 (m, 6H), 0.96-0.77 (m, 15H); ESI-MS: m/z 942.03 (M+H)$^+$.

Step 2: Synthesis of (1R,3S)-3-((((3aR,5aR,5bR, 7aR,9S,11aR,11bR,13aS)-1-isopropyl-5a,5b,8,8,11a-pentamethyl-3a-(2-methyl-2-(3-phenyl-1H-pyrazole-5-carboxamido) propanamido)-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

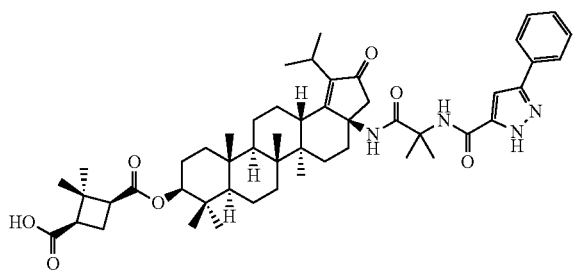

To a stirred solution of 1-benzyl 3-((3aR,5aR,5bR,7aR,9S,11aR,11bR,13aS)-1-isopropyl-5a,5b,8,8,11a-pentamethyl-3a-(2-methyl-2-(3-phenyl-1H-pyrazole-5-carboxamido) propanamido)-2-oxo-3,3a,4,5,5a,5b,6,7,7a,8,9,10, 11,11a,11b,12,13,13a-octadecahydro-2H-cyclopenta[a]chrysen-9-yl)(1R,3S)-2,2-dimethylcyclobutane-1,3-dicarboxylate (step 1, 1.20 g, 1.27 mmol, 1.0 eq) in MeOH (8.5 mL) and THF (8.5 mL) was added aqueous 2.5N KOH solution (3.82 mL, 9.56 mmol, 7.5 eq). The reaction mixture was stirred at room temperature for overnight. After completion of the reaction (monitored by TLC), the organic phase was evaporated under reduced pressure, the reaction mixture was diluted with water (20 mL), cooled to 0° C., pH adjusted to 5.0 with 1N HCl and extracted with DCM (3×50 mL). The combined organic extracts were washed with water (30 mL), dried over sodium sulphate, filtered and evaporated under reduced pressure. The residue was purified by silica gel column chromatography by using 0-4% methanol in dichloromethane gradient. The fractions containing the expected product were combined and concentrated under reduced pressure to obtain the solid. To this solid compound, methyl tert-butyl ether (5 mL) was added and refluxed for about 30 minutes. The mixture was cooled to room temperature; hexane (10 mL) was added, stirred at room temperature for about 2 hours. The solid was filtered, washed with MTBE: hexane (2, 10 ml) and dried under vacuum to obtain the title compound (0.30 g, yield: 27.77%) as an off-white solid. $^1$H NMR (300 MHz, CDCl$_3$): δ ppm 13.6 (bs, 1H), 12.10 (bs, 1H), 8.02 (bs, 1H), 7.80-7.77 (m, 2H), 7.55-7.36 (m, 4H), 7.06 (m, 1H), 4.46 (dd, J=11.1, 4.2 Hz, 1H), 3.11 (m, 1H), 2.81-2.72 (m, 3H), 2.39-2.27 (m, 4H), 2.15-2.09 (m, 1H), 1.92-1.85 (m, 3H), 1.77-1.64 (m, 2H), 1.51 (m, 9H), 1.35-1.21 (m, 8H), 1.15-1.12 (m, 7H), 1.02-0.95 (m, 1H), 0.91-0.78 (m, 20H); ESI-MS: m/z 849.55 (M−H)$^-$.

Pharmacological Activity

The compounds described herein are tested for their antiviral activity following procedures known to a person of ordinary skill in the art. For example, the following protocols can be employed for testing the compounds. These protocols are illustrative and do not limit to the scope of the invention.

Evaluation of Compounds Antiviral Activity

MT2 cells were infected with HIV-1 strain 92HT599 (15TCID 50/30000 cells). The infected cells were plated at the concentration of ~30 000 cells per well in 96 well plate. Test compound was added to the micro plate in defined format with the final concentration of DMSO (vehicle) is not more than 1%. Assay was carried out with and without human serum/human serum albumin (HSA 45 mg/ml) for the serum shift. Incubation was carried out in CO$_2$ incubator for ~96 hours for viral infection. At the end of incubation period an aliquot from each well was taken for p24 estimation. The quantitation of p24 is an index for antiviral activity of the compound. Percent inhibition was calculated with reference to control values (vehicle controls).

P-24 estimation was carried out using Advance biosciences kit as per the procedure detailed by supplier.

For 0% serum binding assay, compounds of the present invention have IC$_{50}$ value of less than 5 nM.

For 45 mg/ml HAS serum binding assay, compounds of the present invention 1-3 have IC$_{50}$ value of less than 50 nM.

REFERENCES

1. Antiviral methods and protocols (Eds: D Kinchington and R. F. Schinazi) Humana Press Inc., 2000.
2. HIV protocols (Eds: N. L. Michael and J. H. Kim) Humana Press Inc, 1999.
3. DAIDS Virology manual from HIV laboratories, Publication NIH-97-3838, 1997.
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:

1. A compound of formula (IA),

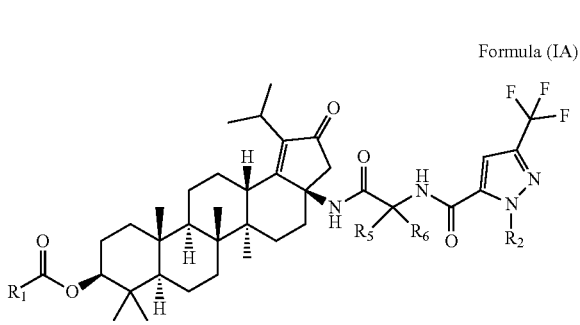
Formula (IA)

wherein $R_1$ is

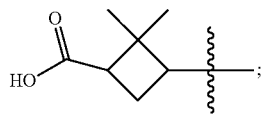 [SMILES: *C1CC(C(=O)O)C1(C)C]

$R_2$ is hydrogen;

$R_5$ and $R_6$ are alkyl;

or pharmaceutically acceptable salts, stereoisomers, or combinations thereof.

2. The compound according to claim 1, which is a compound of formula (IB):

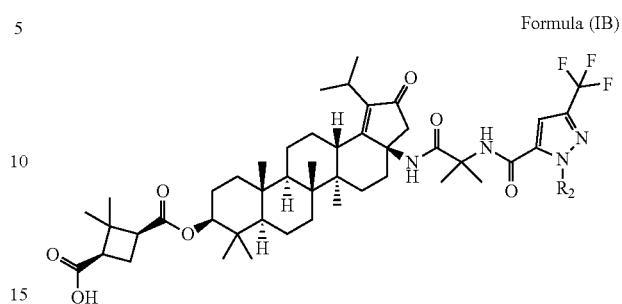
Formula (IB)

wherein, $R_2$ is hydrogen, or pharmaceutically acceptable salts thereof.

3. A compound which is:
(1R, 3S)-3-((((3aR,5aR,5bR,7aR,9S,11aR, 11bR,13aS)-1-isopropyl-5a,5b,8,8,11a-pentamethyl-3a-(2-methyl-2-(3-trifluoromethyl)-1H-pyrazole-5-carboxamido) propanamido)-2-oxo-3,33a, 4,5,5a,5b, 6,7,7a,8,9,10, 11,11a,11b,12,13,13a-octadecahydro-2H-cyclopenta[a]chrysen-9-yl)oxy)carbonyl)-2,2-dimethylcyclobutane-1-carboxylic acid.

4. A pharmaceutical composition comprising the compound according to claim 1 and at least one pharmaceutically acceptable excipient.

5. The pharmaceutical composition according to claim 4, wherein the pharmaceutically acceptable excipient is a carrier or diluent.

* * * * *